United States Patent
Graves et al.

(10) Patent No.: US 10,882,770 B2
(45) Date of Patent: Jan. 5, 2021

(54) BIOGEOCHEMICAL TRANSFORMATIONS OF FLUE GAS DESULFURIZATION WASTE USING SULFUR OXIDIZING BACTERIA

(71) Applicant: Geosyntec Consultants, Inc., Boca Raton, FL (US)

(72) Inventors: Duane Graves, Maryville, TN (US); Allison Kreinberg, Columbus, OH (US); Robby White, Greenville, SC (US); Brianna Wallace, Greenville, SC (US); Brian Adair, Charlotte, NC (US); Linxi Chen, Knoxville, TN (US); Sarah Marie Herr, Central, SC (US)

(73) Assignee: Geosyntec Consultants, Inc., Boca Raton, FL (US)

( * ) Notice: Subject to any disclaimer, the term of this patent is extended or adjusted under 35 U.S.C. 154(b) by 513 days.

(21) Appl. No.: 15/324,320

(22) PCT Filed: Jul. 6, 2015

(86) PCT No.: PCT/US2015/039209
§ 371 (c)(1),
(2) Date: Jan. 6, 2017

(87) PCT Pub. No.: WO2016/007416
PCT Pub. Date: Jan. 14, 2016

(65) Prior Publication Data
US 2017/0203985 A1    Jul. 20, 2017

Related U.S. Application Data

(60) Provisional application No. 62/021,505, filed on Jul. 7, 2014.

(51) Int. Cl.
| | | |
|---|---|---|
| C02F 3/34 | (2006.01) | |
| C01F 11/46 | (2006.01) | |
| B01D 53/84 | (2006.01) | |
| B01D 53/96 | (2006.01) | |
| B01D 53/48 | (2006.01) | |
| C02F 3/02 | (2006.01) | |
| C12N 1/20 | (2006.01) | |
| C12N 1/24 | (2006.01) | |
| C12P 3/00 | (2006.01) | |
| C02F 101/10 | (2006.01) | |

(52) U.S. Cl.
CPC .............. *C02F 3/345* (2013.01); *B01D 53/48* (2013.01); *B01D 53/84* (2013.01); *B01D 53/96* (2013.01); *C01F 11/46* (2013.01); *C02F 3/02* (2013.01); *C12N 1/20* (2013.01); *C12N 1/24* (2013.01); *C12P 3/00* (2013.01); *B01D 2251/404* (2013.01); *B01D 2251/95* (2013.01); *B01D 2258/0283* (2013.01); *C02F 2101/101* (2013.01); *Y02A 50/20* (2018.01)

(58) Field of Classification Search
CPC ...... C02F 3/345; C02F 3/02; C02F 2101/101; B01D 53/84; B01D 53/96; B01D 53/48; B01D 2258/0283; B01D 2251/404; B01D 2251/95; C12N 1/20; C12N 1/24; C12P 3/00; C01F 11/46; Y02A 50/20
See application file for complete search history.

(56) References Cited

U.S. PATENT DOCUMENTS

| | | | | |
|---|---|---|---|---|
| 4,487,784 A | * | 12/1984 | Kuroda ................. | C01F 11/464 106/752 |
| 4,968,622 A | | 11/1990 | Berzaczy et al. ............. | 435/266 |
| 5,296,111 A | * | 3/1994 | Suzuki .................. | C02F 3/1231 205/742 |
| 5,814,514 A | | 9/1998 | Steffan et al. ................ | 435/262 |
| 2002/0189998 A1 | * | 12/2002 | Haase ....................... | C02F 1/52 210/611 |
| 2011/0024363 A1 | * | 2/2011 | Xin ......................... | C04B 11/02 210/742 |
| 2011/0201089 A1 | * | 8/2011 | Burgard ............... | C12N 9/0006 435/243 |
| 2013/0164810 A1 | | 6/2013 | Warkentin et al. .......... | 435/168 |

FOREIGN PATENT DOCUMENTS

| | | | | |
|---|---|---|---|---|
| CN | 1861279 A | | 11/2006 | ............... B09C 1/00 |
| CN | 103043779 A | * | 4/2013 | |
| WO | WO 2008/121079 A1 | | 10/2008 | .............. C02F 11/02 |

OTHER PUBLICATIONS

CN103043379. Apr. 2013. English Machine Translation. (Year: 2013).*
Southerland, WM et al. Sulfite oxidase activity in Thiobacillus novellus. Journal of Bacteriology. 1983. 156(2): 941-944. (Year: 1983).*
Ghosh, W et al. FEMS MIcrobiol. Rev. 2009. 33: 999-1043. (Year: 2009).*
Brown, BP et al. Microbial communities associated with wet flue gas desulfurization systems. Frontiers in Microbiology. 2012. 3: 412. 16 pages. (Year: 2012).*
Spring, S et al. *Limnobacter thiooxidans* gen. nov., sp. nov., a novel thiosulfate-oxidizing bacterium isolated from freshwater lake sediment. International Journal of Systematic and Evolutionary Microbiology. 2001. 51: 1463-1470. (Year: 2001).*

(Continued)

*Primary Examiner* — Renee Claytor
*Assistant Examiner* — Susan E. Fernandez
(74) *Attorney, Agent, or Firm* — Sunstein LLP

(57) ABSTRACT

In some embodiments, the invention provides a method for converting of a flue gas desulfurization (FGD) waste product to a gypsum-enriched product by fostering growth of sulfur oxidizing bacteria (SOB) in the FGD waste product. Also provided are isolated sulfur oxidizing bacteria cultures as well as kits comprising an isolated sulfur oxidizing bacteria culture and written instructions for fostering the growth of the isolated sulfur oxidizing bacteria culture in FGD waste product to product a gypsum-enriched product.

14 Claims, 9 Drawing Sheets

(56) References Cited

OTHER PUBLICATIONS

Friedrich et al., "Oxidation of Reduced Inorganic Sulfur compounds by Bacteria: Emergence of a Common Mechanism," Applied and Environmental Microbiology, vol. 67, No. 7, pp. 2873-2882, 2001.
International Searching Authority, International Search Report, International Application No. PCT/US2015/039209, together with the Written Opinion, 11 pages, dated Oct. 8, 2015.

\* cited by examiner

BIOGEOCHEMICAL TRANSFORMATIONS OF FLUE GAS DESULFURIZATION WASTE USING SULFUR OXIDIZING BACTERIA

REFERENCE TO RELATED APPLICATION

This patent application claims benefit of U.S. provisional application Ser. No. 62/021,505, filed Jul. 7, 2014, the entire contents of which is hereby incorporated by reference.

TECHNICAL FIELD

The present invention relates to treatment processes for altering the chemical composition of industrial waste. In particular, the invention relates to utilizing sulfur oxidizing bacteria to treat industrial waste and produce a usable product.

BACKGROUND ART

Sulfur oxidizing bacteria (SOB) are a diverse group of bacteria that facilitate the oxidation of reduced forms of sulfur to sulfate (see, e.g., Friedrich, C. G., *Adv. Microb. Physiol.* 39: 235-289, 1998). SOB may be autotrophic or chemolithoautotrophic, mixotrophic, photoautotrophic, or heterotrophic and either aerobic or anaerobic. The process of converting reduced forms of sulfur into oxidized forms such as sulfate generates the energy necessary for microbial growth. In the case of autotrophic, phototrophic and chemolithoautotrophic SOB, the sulfur oxidation process provides the energy to convert carbon dioxide into organic compounds that are subsequently used for biosynthesis. SOB are common in nature where they are a key component of the natural biogeochemical sulfur cycle. In addition to the beneficial aspects of their function, they are a cause of acid mine drainage.

Although the physiology of SOB has been studied, their application for industrial purposes is limited. It would therefore be useful to find a role for SOB in industrial or practical settings.

SUMMARY OF THE EMBODIMENTS

In some embodiments, the invention provides processes for altering the chemical composition of flue gas desulfurization (FGD) solid and liquid wastes produced, among other places, at coal-fired, electricity generating power plants, utilizing sulfur oxidizing bacteria (SOB). The alteration changes the FGD waste into a usable gypsum-enriched product.

In a first aspect, the invention provides a method for converting an FGD waste product into a gypsum-enriched product, the method comprising fostering growth of sulfur oxidizing bacteria in the FGD waste product under conditions whereby the sulfur oxidizing bacteria convert sulfite in the FGD waste product to produce a gypsum-enriched product.

In some embodiments, fostering growth of sulfur oxidizing bacteria includes supplementing the FGD waste product with an SOB growth medium. In some embodiments, fostering growth of sulfur oxidizing bacteria includes supplementing the FGD waste product with a sulfur oxidizing bacteria culture wherein the sulfur oxidizing bacteria culture is an isolated SOB culture or a recycled sulfur oxidizing bacteria biomass from a previously treated batch of FGD waste product. In some embodiments, fostering growth of sulfur oxidizing bacteria includes supplementing the FGD waste product with both an SOB growth medium and a sulfur oxidizing bacteria culture (e.g., an isolated sulfur oxidizing bacterial culture).

In some embodiments, the FGD waste product is supplemented with at least $1 \times 10^7$ cells of the isolated sulfur oxidizing culture. In some embodiments, the FGD waste product is selected from the group consisting of an FGD waste-containing slurry, FGD waste in a solid state, and wastewater containing FGD solids. In some embodiments, the conditions comprise fostering growth at a temperature between about 25° C. to about 35° C. In some embodiments, the conditions comprise fostering growth in a presence of ammonium, phosphate, and oxygen. In some embodiments, the conditions comprise a pH of between about 5 to about 8.

In another aspect, the invention provides an isolated sulfur oxidizing bacteria culture, wherein the culture is produced by propagation in sulfur-supplemented SOB growth medium for at least fifteen generations. In some embodiments, the culture is propagated in sulfur-supplemented SOB growth medium for at least twenty generations. In some embodiments, the culture converts sulfite to sulfate in a sulfur-supplemented SOB growth medium at the rate of at least 0.1% per day. In some embodiments, the culture converts sulfite to sulfate in a sulfur-supplemented SOB growth medium at the rate selected from the group consisting of at least 0.25% per day, at least about 0.5% per day, and at least about 0.75% per day. In some embodiments, the culture converts sulfite to sulfate in a biostimulated FGD slurry at least 1.5 times faster than endogenous SOB in the FGD slurry. In some embodiments, the culture converts sulfite to sulfate in a biostimulated FGD slurry at least two times faster than endogenous SOB in the FGD slurry.

In another aspect, the invention provides a kit comprising an isolated sulfur oxidizing bacteria culture, and written instructions for bioaugmenting FGD waste product to produce a gypsum-enriched product. In some embodiments, the kit further comprises SOB growth medium. In some embodiments, the kit further comprises sulfur-supplemented SOB growth medium.

BRIEF DESCRIPTION OF THE DRAWINGS

The foregoing features of embodiments will be more readily understood by reference to the following detailed description, taken with reference to the accompanying drawings, in which:

(FIG. 8A) or room temperature (i.e., 20° C.; FIG. 8B).

DETAILED DESCRIPTION OF SPECIFIC EMBODIMENTS

Figure 1:
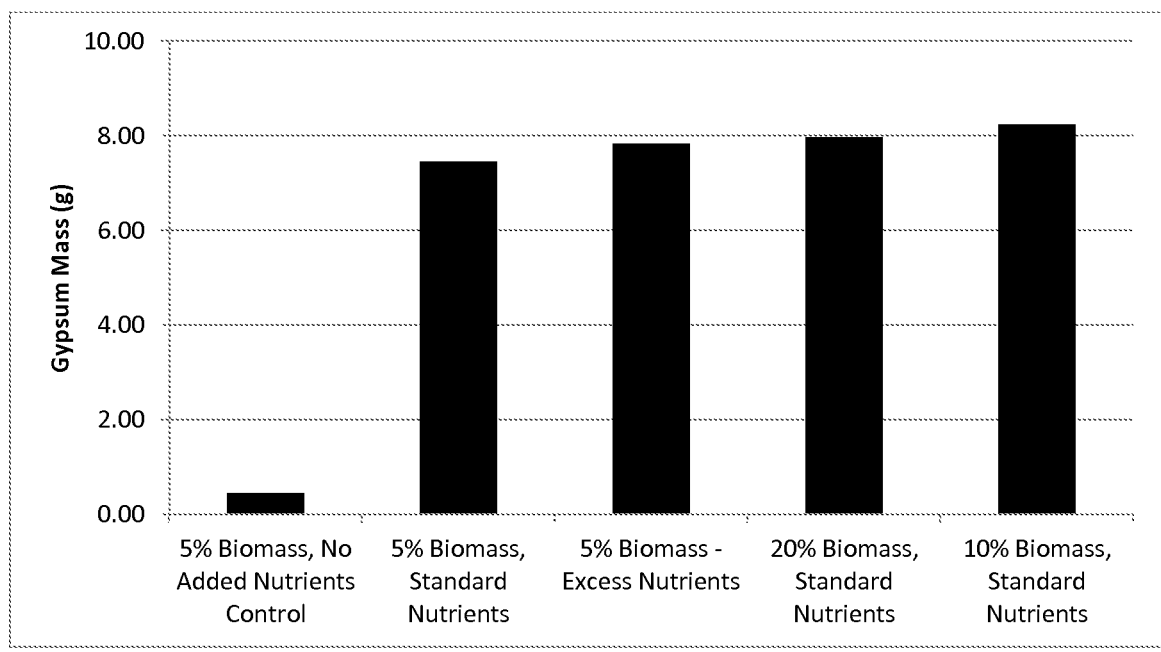
FIG. 1 is a bar graph showing the effect of adding isolated SOB culture to nutrient amended (biostimulated) FGD waste for the purpose of evaluating enhanced conversion of calcium sulfite hemihydrate (hannebachite) to calcium sulfate dihydrate (gypsum) in the presence of active isolated SOB culture. Gypsum formation is normalized to 100 g FGD waste in FIG. 1. Using a biosolids recycling method common in bioreactor operation, the isolated SOB culture was added as 5% by volume of the previously treated bioreactor contents, which had been bioaugmented with solids-free liquid culture. As can be seen, when the isolated SOB culture is added with only aerated water (bar labeled "5% Biomass, No Added Nutrients Control"), there is very little gypsum conversion because the activity of the isolated SOB culture was limited by the lack of nutrients. However, when standard nutrients (i.e., the normal concentration of SOB growth medium containing mostly ammonium and phosphate and minor amounts of other inorganic nutrients) or excess nutrients (i.e., the SOB growth medium at higher than normal concentration to primarily increase the amount of available ammonium and phosphate) are added with aeration (to provide oxygen), the increase in the activity of the isolated SOB culture (as measured by gypsum production) is dramatic. Notably, there is an amount of nutrients that is beneficial for gypsum formation but excessive amounts of nutrients do not further enhance gypsum formation.

The present invention is based upon the development of methods and systems for the production of gypsum in solid and liquid (wastewater) FGD waste utilizing sulfur oxidizing bacteria (SOB). The gypsum thus produced has multiple well-known uses (e.g., as a component of plaster, a component of dry wall, a soil amendment for certain crops such as peanuts, a component of cement, a coagulant (and provider of dietary calcium in tofu), an ingredient for making mead, etc.).

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

Likewise, any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As described above, sulfur oxidizing bacteria (SOB) convert reduced forms of sulfur into oxidized forms. Several potential applications for using sulfur oxidizing bacteria have been evaluated. For example, they have been tested for their ability to remove sulfur from coal. Sulfur oxidizing bacteria have been evaluated as a catalyst to acidify soil for the purpose of remediating soil contaminated with radionuclides and heavy metals. They may be used to remove hydrogen sulfide from anaerobic waste streams. Bioleaching of metals from ore is an application that has been applied at large scale. Metal sulfide minerals are oxidized by SOB for the purpose of dissolving and recovering the metal.

The present invention relates, in part, to using sulfur oxidizing bacteria to treat FGD waste. Analytical methods for quantifying the composition of FGD waste require testing using X-ray diffraction to semi-quantitatively identify chemical components of FGD waste and thermogravimetric measurement of FGD waste to detect and quantify calcium sulfite hemi-hydrate and gypsum (calcium sulfate dihydrate). Residual calcium carbonate may be analyzed titrimetrically. Impurities such as metals and organics are analyzed by various spectrometric and chromatographic methods.

Analytical methods for quantifying biomass (number of cells) in reaction mixtures include measurement of volatile solids, growth of bacteria on solid medium (plate counts), most probable numbers estimations, quantitation of biological molecules such as protein, nucleic acid and adenosine triphosphate (ATP), direct microscopic counting, automated cell counting, and respiration rate.

As used herein, an "FGD waste product" means flue gas desulfurization wastes in the form of a slurry, or in a solid state, or in wastewater, produced, among other places, at coal-fired, electricity generating power plants. Note that the FGD waste product that is a slurry is a mixture of FGD waste product with a liquid that is not SOB growth medium or a sulfur-supplemented SOB growth medium. Such a liquid that is not a SOB growth medium or a sulfur-supplemented SOB growth medium can include water, oil, various mixtures of same, and the like.

In some embodiments, where a slurry of a FGD waste product is made by supplementing FGD waste product with sulfur-supplemented SOB growth medium, the resulting FGD slurry is referred to as a "biostimulated FGD waste product".

As used herein, an "SOB growth medium" is a mixture of components that provides nutrients to enable growth of sulfur oxidizing bacteria. Generally, SOB growth medium contains a source of ammonium (e.g., $(NH_4)_2Fe(SO_4)_2 \cdot 6H_2O$ or $NH_4Cl$) and a source of phosphorus (e.g., $K_2HPO_4$). In some embodiments, the SOB growth medium further comprises a source of iron (e.g., $FeCl_3$ or $(NH_4)_2Fe(SO_4)_2 \cdot 6H_2O$ or $FeSO_4$). In some embodiments, the SOB growth medium further comprises, a source of potassium (e.g., $K_2HPO_4$). In some embodiments, the SOB growth medium may also contain a source of micronutrients including magnesium (e.g., $MgSO_4 \cdot 7H_2O$). In some embodiments, the SOB growth medium may also contain a source of manganese (e.g., $MnSO4 \cdot 2H_2O$). An example of such a recipe is the Starkey's Medium. One description of this medium is provided in Charles and Suzuki, "Mechanism of thiosulfate oxidation by *Thiobacillus novellus*," *Biochimica et Biophysica Acta (BBA)-Enzymology and Biological Oxidation* 128 (3): 510-521, 1966. Other sources for descriptions of such an SOB growth medium are well known.

One non-limiting recipe for making the SOB growth medium is as follows: Dissolve about 0.2 to about 0.4 grams $(NH_4)_2SO_4$, about 3.0 to about 4.0 g $KH_2PO_4$, about 0.02 g $CaCl_2 \cdot 2H_2O$, about 0.5 g $MgSO_4 \cdot 7H_2O$, and about 0.01 g $FeSO_4$ in 1 liter of water, or add water such that the total volume of the medium is 1 liter.

Another non-limiting recipe for making the SOB growth medium is as follows: Measure out about 4 g $K_2HPO_4$, about 1.5 g $KH_2PO_4$, about 0.02 g $CaCl_2 \cdot 2H_2O$, about 0.1 g $MgSO_4 \cdot 7H_2O$, about 0.3 g $(NH_4)_2SO_4$, about 0.02 g $MnSO_4 \cdot 2H_2O$, about 0.02 g $FeCl_3 \cdot 6H_2O$ and add water to 1 liter.

In some embodiments, sulfur is added to SOB growth medium to produce "sulfur-supplemented SOB growth medium". Such sulfur-supplemented SOB growth medium media is simply SOB growth medium to which a source of reduced sulfur has been added. For example, $Na_2S_2O_3 \cdot 5H_2O$ or $CaSO_3 \cdot \frac{1}{2}H_2O$ are non-limiting reduced sulfur sources.

One non-limiting recipe for making the sulfur-supplemented SOB growth medium is as follows: Measure out about 4 g $K_2HPO_4$, about 1.5 g $KH_2PO_4$, about 0.02 g $CaCl_2 19 \, 2H_2O$, about 0.1 g $MgSO_4 \cdot 7H_2O$, about 0.3 g $(NH_4)_2SO_4$, about 0.02 g $MnSO_4 \cdot 2H_2O$, about 0.02 g $FeCl_3 \cdot 6H_2O$ and add water to 1 liter, and then add about 10 g of $Na_2S_2O_3 \cdot 5H_2O$ or 10 g of $CaSO_3 \cdot 0.5H_2O$.

"SOB" or "sulfur oxidizing bacteria" are organisms in the domains of Archaea and Bacteria that oxidize sulfur. In some embodiments, the SOB oxidize reduced inorganic sulfur compounds. An SOB culture means a culture (or population) of sulfur oxidizing bacteria, and an SOB growth medium simply means a medium in which sulfur oxidizing bacteria can grow. In some embodiments, the sulfur oxidizing bacteria is chemolithoautotrophic (i.e., the organism obtains carbon from carbon dioxide).

By "fostering growth of sulfur oxidizing bacteria" in an FGD waste product means at least one of (a) supplementing the FGD waste product with an SOB growth medium to provide SOB nutrients and (b) supplementing the FGD waste product with an SOB culture or an isolated SOB culture (e.g., an actively growing culture or simply an "active" culture).

Embodiments of the present invention achieve treatment of an FGD waste product by using sulfur oxidizing bacteria to convert calcium sulfite into calcium sulfate (e.g., via biogeochemical conversion) for the purpose of increasing the gypsum content (i.e., a mineral composed of calcium sulfate dihydrate and possibly calcium sulfate anhydrate and calcium sulfate hemihydrate)) and reducing the calcium sulfite hemihydrate content of FGD waste. The sulfur oxidizing bacteria provide an additional benefit in that certain strains of SOB (including the ones described herein) can use carbon dioxide or carbonate for growth. The carbon dioxide or carbonate may be obtained from residual limestone in the FGD waste or the atmosphere. As noted below, although sulfur oxidizing bacteria can use carbonate for growth, the sulfur oxidizing bacteria would rather use carbon dioxide. However, in carbon dioxide-free environments, sulfur oxidizing bacteria can also use carbonate which is present in FGD waste.

Thus, in a first aspect, the invention provides a method for converting a FGD waste product into a gypsum-enriched product, comprising fostering growth of sulfur oxidizing bacteria in the FGD waste product under conditions whereby the sulfur oxidizing bacteria convert sulfite in the FGD waste product to produce a gypsum-enriched product.

In some embodiments, fostering growth of sulfur oxidizing bacteria may include simply biostimulating the FGD waste with the addition to the FGD waste of SOB growth medium to stimulate growth of endogenous SOB in the waste. In some embodiments, fostering growth of sulfur oxidizing bacteria includes both biostimulating the FGD waste and bioaugmenting the FGD waste with the addition of isolated SOB culture. In some embodiments, the isolated SOB culture is active.

The sulfur oxidizing bacteria used for FGD waste product conversion may be enriched and derived from a variety of sources. Some non-limiting sources include, for example, actual FGD waste product from a coal-fired generating plant, soil around coal piles, agricultural soil, slightly acidic soil in which acid-loving crops (e.g., tomatoes) have been grown, and garden soil. The sulfur oxidizing bacteria (SOB) culture described herein were enriched and derived from samples using a chemostat. Cell densities approaching 1 billion cells per milliliter are achieved in the SOB chemostats. During enrichment and subsequent propagation (i.e., rapidly grown), the SOB were provided a sulfur-supplemented SOB growth medium that supplies their nutritional needs. Note that when the SOB were propagated in SOB growth medium that did not include FGD waste, the SOB growth medium was supplemented with a form of reduced sulfur such as elemental sulfur, sulfide, thiosulfate, or sulfite. This SOB growth medium is referred to as "sulfur-supplemented SOB growth medium". In some embodiments, when the SOB are first enriched from the source (e.g., FGD waste or soil), they may be initially propagated in sulfur-supplemented SOB growth medium.

After enrichment and propagation in sulfur-supplemented SOB growth medium, the enriched population (or culture) will have undergone selection (which may include selection for random mutations) to favor those most able to (a) grow rapidly in the sulfur-supplemented SOB growth medium and (b) convert the highest amount of sulfite to sulfate in the sulfur-supplemented SOB growth medium. Generally, such selections are stabilized in a culture after about fifteen to about twenty generations following enrichment from the source (e.g., FGD waste product or from garden soil). Thus, after enrichment from the source and after propagation for at least about fifteen to at least about twenty generations in the sulfur-supplemented SOB growth medium, the SOB culture will be referred to as an "isolated SOB" culture. Note that the terms "propagate" and "propagation" are used herein to refer to growth of SOB under conditions whereby the cells of the SOB are actively and rapidly dividing or doubling. In contrast, "growth" (as in "fostering growth") means the growth of SOB in optimal or sub-optimal conditions where the at least some cells of the SOB are dividing, but not necessarily at a rapid rate.

Figure 2A:
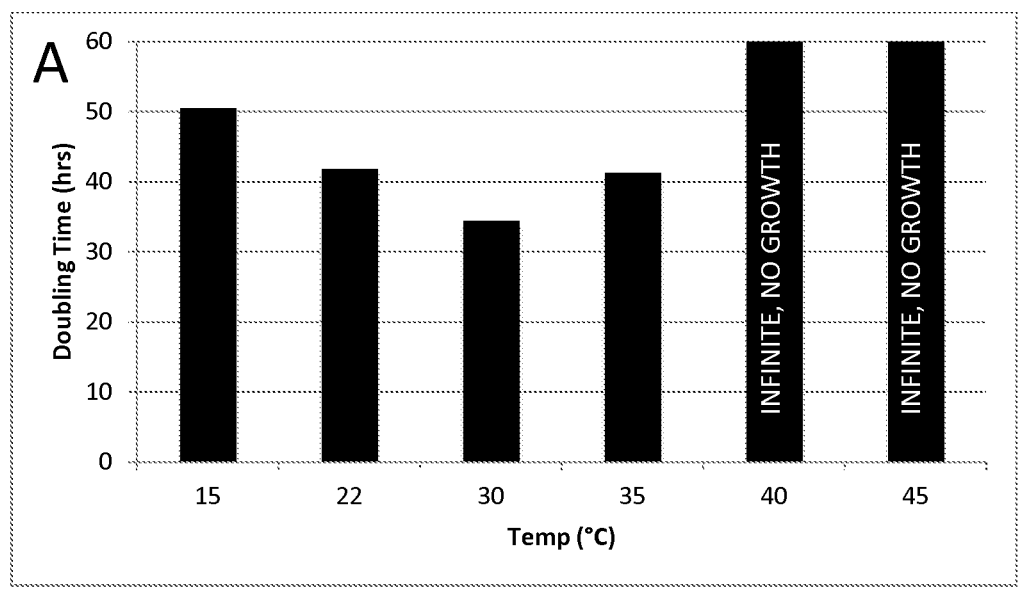
FIGS. 2A and 2B are bar graphs demonstrating the temperature preference of the isolated SOB culture at which the culture achieves the highest growth rate as shown in doubling time (FIG. 2A) and in growth rate per hour (FIG. 2B). As shown, at approximately 30° C., the isolated SOB culture showed the fastest doubling time (35 hours in FIG. 2A) and the fastest growth rate (0.02 per hour in FIG. 2B).

Since bacteria growth occurs rapidly when propagated under optimal conditions (e.g., see FIG. 2A, where the optimal doubling time or generation at 30° C. is 35 hours), an isolated SOB culture can be defined as an SOB culture grown in a sulfur-supplemented SOB growth medium for at least 22 days, or at least 29 days, or at least 25.5 days. It will be understood that once the SOB culture has become isolated (i.e., once it has been enriched from its source and grown in sulfur-supplemented SOB growth medium for at least 22 days), it can be stored and still remain isolated. The isolated SOB culture can be stored by any means known in the art (e.g., streaked onto agar plates, as a bacterial stab or frozen in liquid nitrogen or on dry ice). The isolated SOB culture can also be used to treat FGD waste and, once recycled as biomass from treated FGD waste, still be considered isolated. Thus, as described below in Table 1, the recycled SOB biomass is isolated SOB culture even though there is not an additional propagation step between the treated FGD waste (from which the isolated SOB culture biomass was recycled) and the new FGD waste to which the recycled isolated SOB culture biomass is being added.

Thus, in another aspect, the invention provides an isolated SOB culture. In some embodiments, the isolated SOB culture may be maintained or stored in sulfur-supplemented SOB growth medium.

In some embodiments, an isolated SOB culture is able to produce at least about 0.1% sulfate per day from either sulfur-supplemented SOB growth medium or biostimulated FGD waste product. In some embodiments, an isolated SOB culture is able to produce at least about 0.2% sulfate per day, or at least about 0.5% sulfate per day, or at least about 1.0% sulfate per day from either sulfur-supplemented SOB growth medium or biostimulated FGD waste product.

In some embodiments, an isolated SOB culture is able to deplete at least about 0.1% sulfite per day from either sulfur-supplemented SOB growth medium or biostimulated FGD waste product. In some embodiments, an isolated SOB culture is able to deplete at least about 0.2% sulfite per day, or at least about 0.5% sulfite per day, or at least about 1.0% sulfite per day from either sulfur-supplemented SOB growth medium or biostimulated FGD waste product.

The isolated SOB cultures are used to bioaugment FGD wastes to stimulate sulfite oxidation after nutrients requirements have been satisfied (see, e.g., FIG. 1) and to enhance the rate of oxidation. When FGD waste is supplemented with isolated SOB culture, the FGD waste is referred to as "bioaugmented" FGD waste.

FIG. 1 shows the enhanced rate of calcium sulfite hemihydrate (hannebachite) conversion to calcium sulfate dihydrate (gypsum) in FGD waste when isolated SOB culture and SOB growth medium are added to the FGD waste. As can be seen in FIG. 1, simply adding 5% by volume isolated SOB culture (from a recycled biomass containing more than $1 \times 10^7$ cells per milliliter (mL)) in water and without SOB growth medium (nutrients) results in minimal production of gypsum. However, when the 5% biomass containing the isolated SOB culture is added to the FGD treatment with SOB growth medium, a dramatic increase in gypsum production was observed over 5-10 days of treatment of the FGD waste at room temperature in the presence of oxygen. The SOB growth medium used in FIG. 1, second bar, was made using the formula: 4 g $K_2HPO_4$, 1.5 g $KH_2PO_4$, 0.02 g $CaCl_2 \cdot 2H_2O$, 0.1 g $MgSO_4 \cdot 7H_2O$, 0.3 g $(NH_4)_2SO_4$, 0.02 g $MnSO_4 \cdot 2H_2O$, 0.02 g $FeCl_3 \cdot 6H_2O$ in 1 liter of water. Interestingly, when a 2× growth medium is used (e.g., 4 g $K_2HPO_4$, 1.5 g $KH_2PO_4$, 0.02 g $CaCl_2 \cdot 2H_2O$, 0.1 g $MgSO_4 \cdot 7H_2O$ 0.3 g $(NH_4)_2SO_4$, 0.02 g $MnSO_4 \cdot 2H_2O$, 0.02 g $FeCl_3 \cdot 6H_2O$ in 0.5 liters of water), the rise is gypsum production is negligible (compare the $2^{nd}$ and $3^{rd}$ bars in FIG. 1). Likewise, adding more isolated SOB culture (in the form of an increased percent of recycled biomass) resulted in only a negligible increase in gypsum production (compare the $2^{nd}$ bar to the $4^{th}$ and $5^{th}$ bars in FIG. 1).

as compared to the FGD waste supplemented with additional nutrients in the added SOB growth medium that stimulate the activity of the isolated SOB culture and results in a greater gypsum product yield.

In some embodiments, the sulfur oxidizing bacteria used to bioaugment FGD waste are SOB recycled from a previously treated batch of FGD waste product.

Figure 2B:
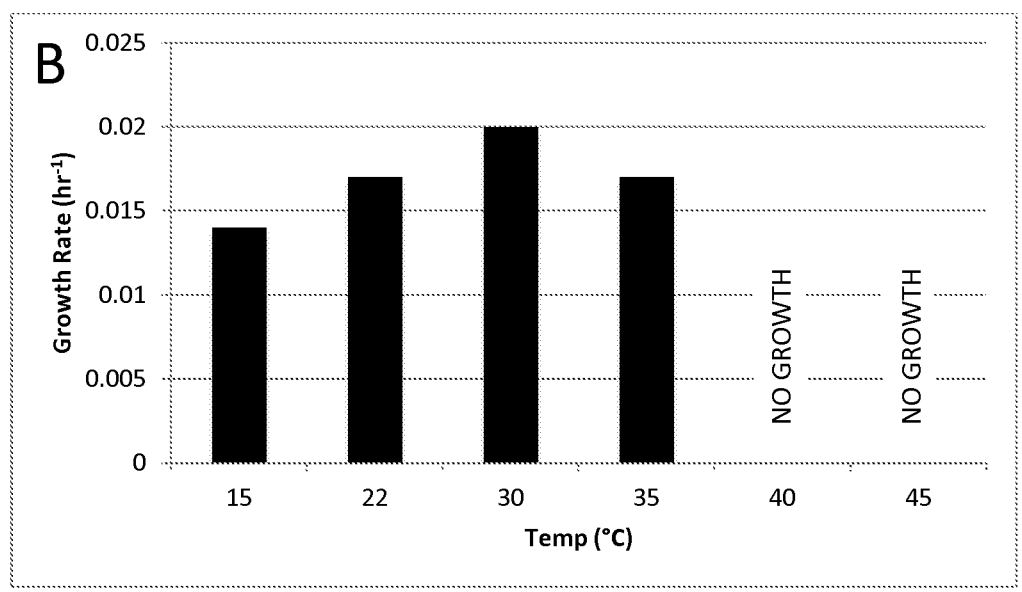
Figure 3:
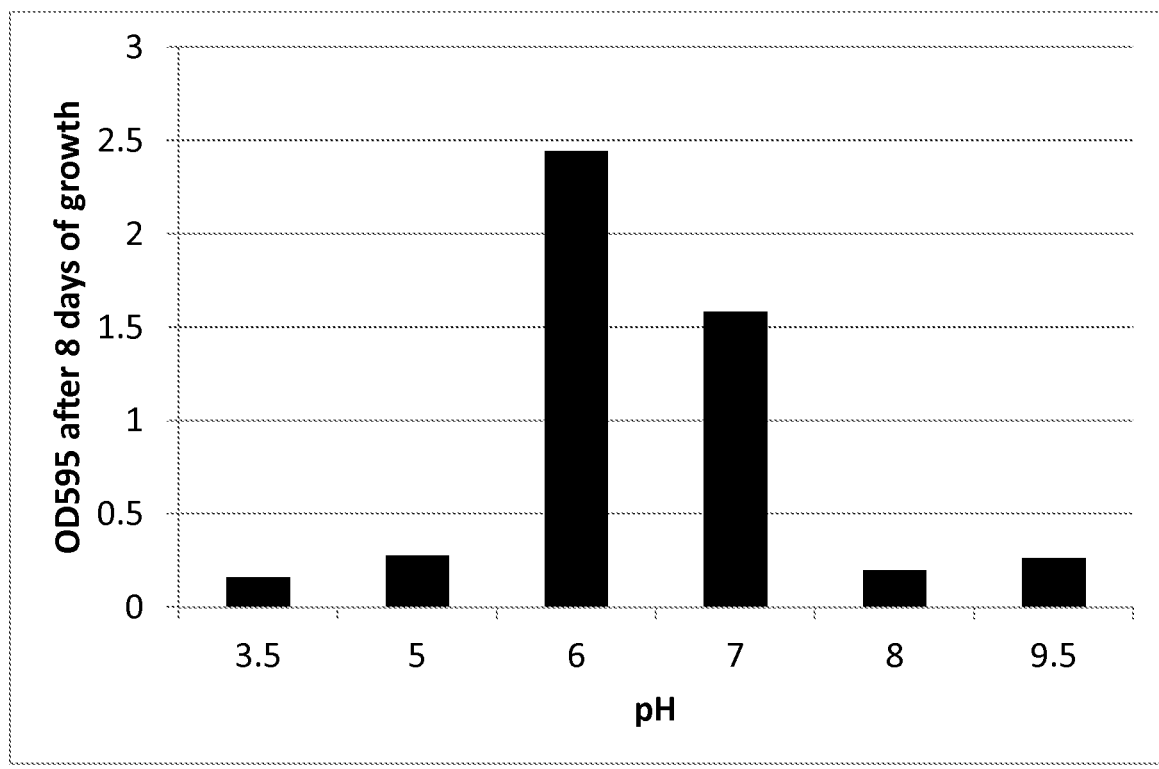
FIG. 3 is a bar graph illustrating the growth of SOB culture at various pH values. As shown, the optimal pH for fastest growth of isolated SOB culture is in the range of pH 6 to 7 although some SOB are known to thrive in much more acidic environments. The neutrophilic habit of the isolated SOB is important for their function in FGD waste, which may have a neutral to alkaline pH.
Figure 4:
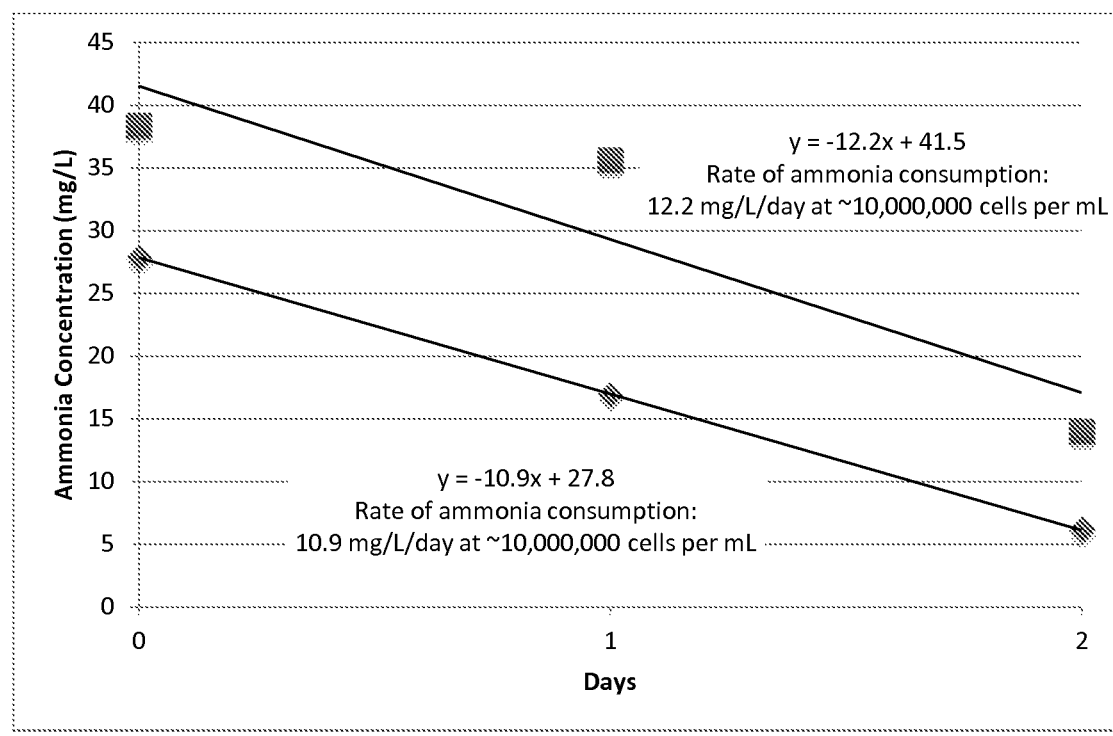
FIG. 4 is a line graph that demonstrates the consumption of fixed nitrogen (ammonia) during isolated SOB culture growth. As shown, approximately $10^7$ cells require between about 10.8 milligrams per liter of culture per day (mg/L/day) to about 12.3 mg/L/day of ammonia.
Figures 5A, 5B, 5C:
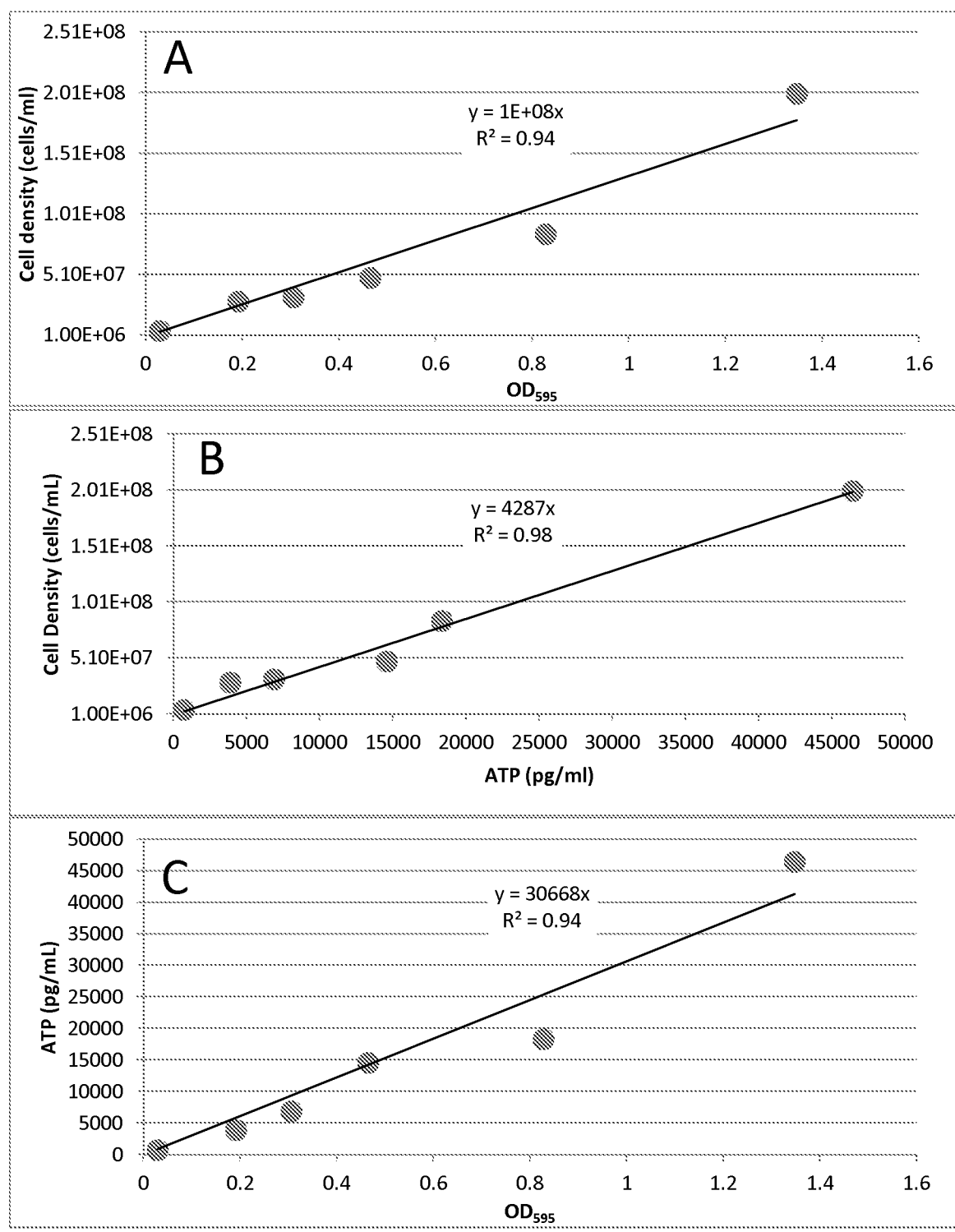
FIGS. 5A-5C are a series of line graphs showing the correlation of optical density of isolated SOB culture cell density with ATP concentration. As FIGS. 5A-5C show, $5.1 \times 10^7$ cells have an optical density (OD) measured at a wavelength of 595 nanometers (nm) (OD595) of about 0.4, and produce approximately 12500 picograms per milliliter (pg/ml) of ATP. Likewise, $1.01 \times 10^8$ cells have an optical density at OD595 of about 0.8, and produce approximately 23,000 pg/ml of ATP.

To convert sulfite to sulfate, the SOB require specific conditions that include a temperature below 40° C. with best SOB growth occurring when the temperature is about 30° C. (see FIGS. 2A and 2B); provision of ammonium, phosphate, and oxygen; and a pH above 5 and less than 8 with a preference for pH 6 to 7 (FIG. 3). As shown in FIG. 4, the ammonium requirement is approximately 11 to 12 mg/L per $10^7$ cells. Phosphate is required but the demand is low. Aeration is adjusted to provide dissolved oxygen. Bioaugmentation with SOB culture is beneficial (FIG. 1), especially for treatment of wastes that do not contain endogenous SOB and/or FGD waste that may not have a highly active natural SOB population. Because of the high solids concentration that is unstable at the temperature used for volatile solids measurement and the poor growth of the SOB on solid culture medium (agar plates), which eliminated the plate counting method, common methods of biomass quantification were found to be unreliable. Therefore, adenosine triphosphate (ATP) concentration was used to reliably estimate biomass (i.e., the number of cells) as shown in FIGS. 5A-5C where direct cell counts in cells per milliliter (cells/mL), optical density measured at a wavelength of 595 nanometers (nm) (OD595), and ATP content in picograms per milliliter (pg/mL) were demonstrated to be directly correlated to each other.

Figure 6:
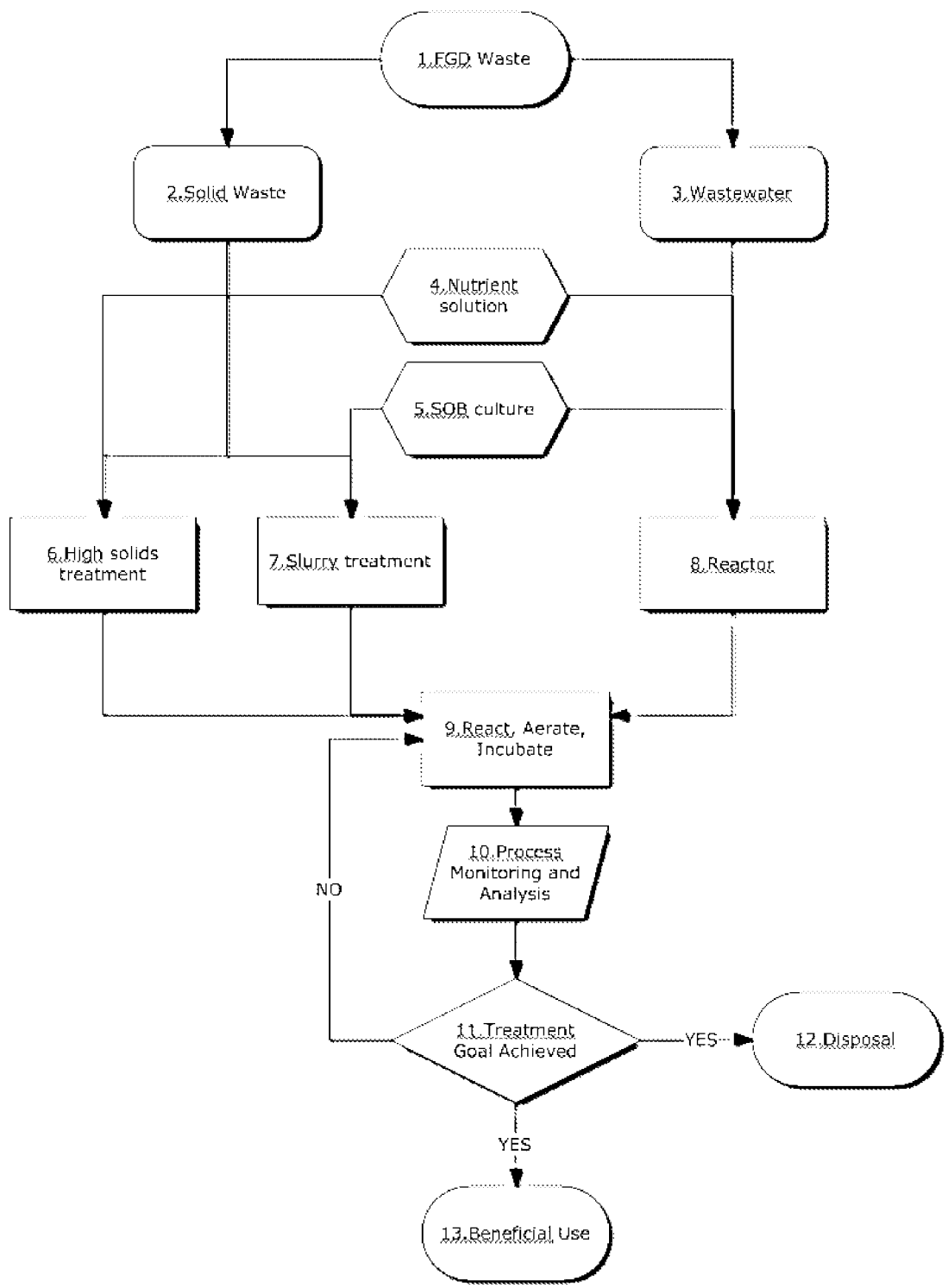
FIG. 6 is a flow diagram illustrating steps in a method for treating FGD waste in accordance with an embodiment of the present invention.

FIG. 6 is a flow diagram illustrating steps in a method for achieving treatment of FGD waste product in accordance with an embodiment of the present invention. In this figure are illustrated treatment processes for solid waste; treated as a slurry with up to 40% solids; and wastewater. Although FIG. 6 pertains to examples of waste slurries, embodiments of the present invention may be used with other forms of FGD waste products as well such as wastewater or wet solids with no drainable water.

For purposes of FIG. 6, the item numbers identify components as follows:
1. FGD Waste Product, FGD waste subject to treatment due to high calcium sulfite concentration.
2. Solid Waste, precipitated waste from the FGD process that is dewatered for storage/disposal/reuse.
3. Wastewater, aqueous waste from the FGD process that contains suspended and dissolved calcium sulfite.
4. Nutrient Solution, a formula of macro and micronutrients comprised of sources of ammonium nitrogen, phosphate, potassium, iron, magnesium and calcium. This is the SOB growth medium without addition of exogenous sulfur.
5. SOB Culture, a liquid suspension of live isolated SOB culture cells growing in nutrient solution (i.e., SOB growth medium) used to bioaugment FGD waste. Note that the isolated SOB culture cells are grown in sulfur-supplemented SOB growth medium. When the isolated SOB culture is added to the FGD to bioagument the FGD waste, there is very little sulfur in the sulfur-supplemented SOB growth medium in which the cells of the isolated SOB culture are suspended. Thus, the sulfur source of the isolated SOB culture in the bio-augmented and biostimulated FGD waste will be the sulfur contaminating the FGD waste itself.
6. High solids treatment, an embodiment of the method where dewatered, damp FGD waste is supplemented with nutrient solution (i.e., SOB growth medium) and/or isolated SOB culture for treatment.
7. Slurry treatment, an embodiment of the method where FGD solid waste is mixed with nutrient solution (i.e., SOB growth medium) and/or isolated SOB culture to form a slurry for treatment.
8. Reactor, an embodiment of the method where FGD wastewater is amended with nutrient solution (i.e., SOB growth medium) and/or isolated SOB culture for sulfite treatment.
9. React, aerate, incubate, the process where FGD waste is treated with nutrient solution (i.e., SOB growth medium) and/or isolated SOB culture, aerated by mixing or air injection, and incubated for a period of time necessary to achieve sulfite conversion and/or limestone removal.
10. Process monitoring and analysis, the process and method where FGD waste undergoing treatment is tested to track treatment progress and verify completion.
11. Treatment goal achieved, the decision point for treatment completion based on step 10 results.
12. Disposal/recycle, the final disposition of FGD waste, especially for treated wastewater that may be discharged, further processed, or recycled for use in the plant.
13. Beneficial use, the final disposition of FGD waste, typically for solids.

Various embodiments of the present invention provide methods of treating a wide range of FGD solid waste products, including slurries, solid waste with minimal water, and FGD wastewater that has low solids content. Embodiments of the invention typically include: (i) the enrichment and sustained propagation of isolated SOB culture(s), (ii) the specific reaction conditions needed to facilitate the sulfite to sulfate conversion, (iii) engineering designs for delivering the technology to various FGD waste forms, and optionally (iv) analytical methods designed to specifically analyze in near-real-time the sulfate, sulfite, and carbonate composition of FGD waste.

Figure 7:
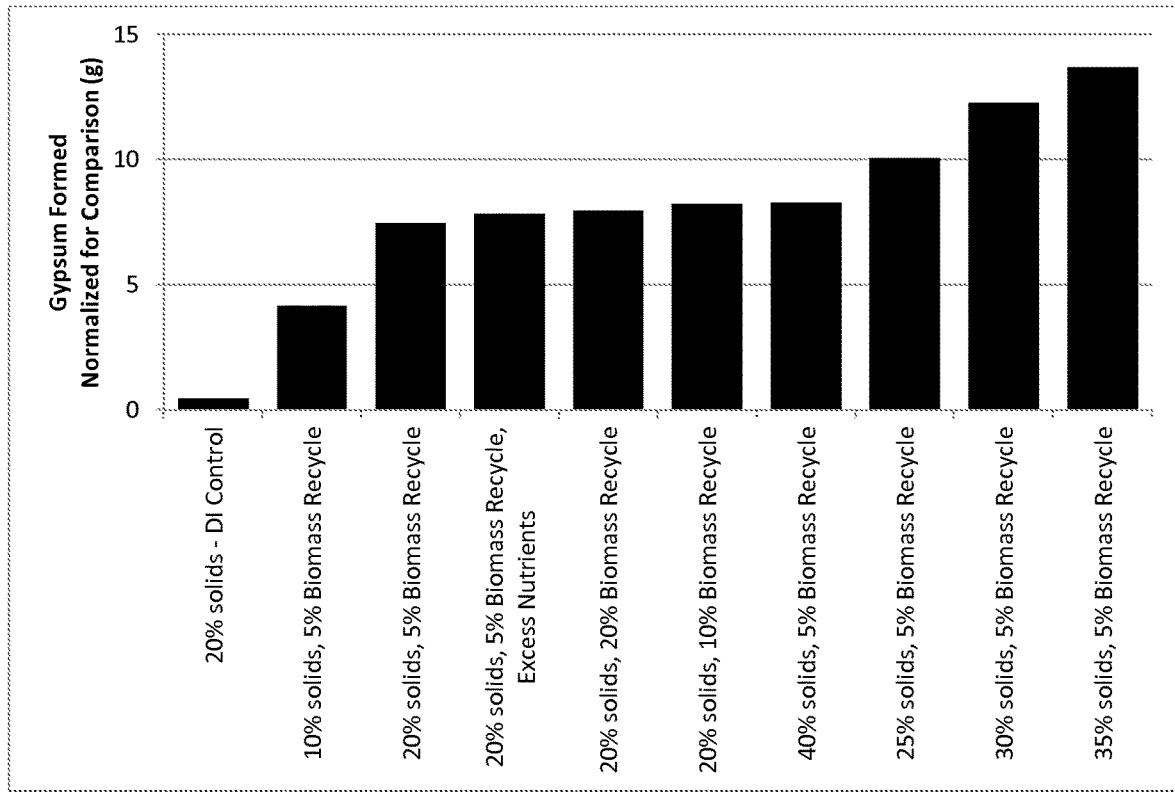
FIG. 7 is a bar graph of results in which is plotted the effect of solids content in treatment reactors on the formation of gypsum after treatment and normalized to 100 g FGD waste, in accordance with embodiments of the present invention. Note that in this figure, "biomass recycle" is used to refer to the isolated SOB culture.

One embodiment of a method in accordance with the present invention includes the application of nutrients to the excavated and slurried FGD waste solids, which are typically granulated, in settling ponds, or other suitable containment beds (which may be specially formed for the purpose), with aeration by mixing or injecting air with various diffusers until the sulfite is converted to sulfate at which time the solids are dewatered and further processed for commercial use. Treatment is performed on batches of FGD waste with the solids content controlled by the ability to mix the slurry and efficiency of treatment. Up to 40% solids are subject to treatment although lower concentrations may have better conversion efficiency (FIG. 7)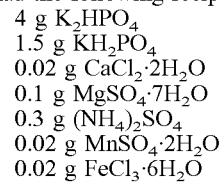. This process can be repeated until the entire mass of the FGD waste has been treated.

In another embodiment, FGD solid waste may be excavated and slurried with SOB growth medium (to become biostimulated), bioaugmented with isolated SOB culture and aerated to stimulate sulfite bio-oxidation to sulfate and possible reduction in calcium carbonate (limestone).

In another embodiment, FGD wastewater treatment by biostimulation and bioaugmentation may be accomplished in a bioreactor operated under aerobic to microaerobic conditions using any aerobic bioreactor design.

In another embodiment, FGD waste treatment may be performed directly in the settling/storage ponds, containment cells, or basins such that nutrients and bioaugmentation solutions are added to the surface of the settled FGD waste, aeration is achieved by tilling, and upon treatment, the treated layer is scrapped off for use and the newly exposed surface is biostimulated with addition of SOB growth medium, bioaugmented with addition of isolated SOB culture, and reacted. This process can be repeated until the entire thickness of the FGD waste has been treated.

In another embodiment, FGD waste may be treated in a slurry formed in the containment cell through nutrient amendment, bioaugmentation, and aeration by mixing or air injection. Upon completion of the reaction, treated material is removed and further processed for commercial application. This process can be repeated until the entire mass of FGD waste has been treated (i.e., biostimulated and/or bioaugmented).

The isolated SOB culture used for bioaugmentation is a consortium of bacteria typically derived from the FGD waste or another source of chemolithoautotrophic SOB. The isolated SOB culture have the characteristics of preferring a near neutral pH, and an optimum reaction temperature of approximately 30 to 35° C.

Example I

To treat FGD waste (and by "treat" is meant biostimulate and/or bioaugment FGD waste product), a biosimulated FGD slurry was made by mixing an amount of FGD waste with SOB growth medium that is not supplemented with a source of sulfur. The SOB growth medium in this example had the following recipe:
4 g $K_2HPO_4$
1.5 g $KH_2PO_4$
0.02 g $CaCl_2 \cdot 2H_2O$
0.1 g $MgSO_4 \cdot 7H_2O$
0.3 g $(NH_4)_2SO_4$
0.02 g $MnSO_4 \cdot 2H_2O$
0.02 g $FeCl_3 \cdot 6H_2O$
With water added to 1 liter.

The isolated SOB culture used in this example were obtained from, propagated, and maintained in sulfur-supplemented SOB growth medium made as follows:
About 4 g $K_2HPO_4$, about 10 g $Na_2S_2O_3 \cdot 5H_2O$, about 1.5 g $KH_2PO_4$, about 0.02 g $CaCl_2 \cdot 2H_2O$, about 0.1 g $MgSO_4 \cdot 7H_2O$, about 0.3 g $(NH_4)_2SO_4$, about 0.02 g $MnSO_4 \cdot 2H_2O$, about 0.02 g $FeCl_3 \cdot 6H_2O$ is measured out and water is added to 1 liter.

Table 1 provides an example of the treatment achieved by the invention. Table 1 includes FGD waste slurry samples treated with (a) exogenously added isolated SOB culture and SOB growth medium ("bioagumented and biosimulated") or (b) only added SOB growth medium ("biostimulated"). For these studies, isolated SOB culture at approximately $10^7$ cells/ml were added as 5% by volume of previously treated FGD waste to carry forward SOB into a new treatment batch containing a slurry of 20% FGD waste mixed into SOB growth medium, where the growth medium was not supplemented with a reduced form of sulfur. The amount of sulfate, sulfite, and carbonate was measured immediately prior to addition of the FGD waste to the SOB growth medium to form a 20% slurry, and measured again 24 days after the FGD slurry had been made. In the bioaugmented and biosimulated group, when the slurry was made, about $10^7$ cells/ml of isolated SOB culture was added, and the amount of sulfate, sulfite, and carbonate was measured immediately. 24 days after preparation of the slurry supplemented with the isolated SOB culture, the amount of sulfate, sulfite, and carbonate was measured again.

In the biosimulated group, the added SOB growth medium will stimulate the growth of endogenous SOB in the FGD waste slurry samples. Thus, Table 1 shows the difference in activity between isolated SOB (in the bioaugmented and biosimulated treatment group) and endogenous SOB (in the biostimulated group).

Figure 8A:
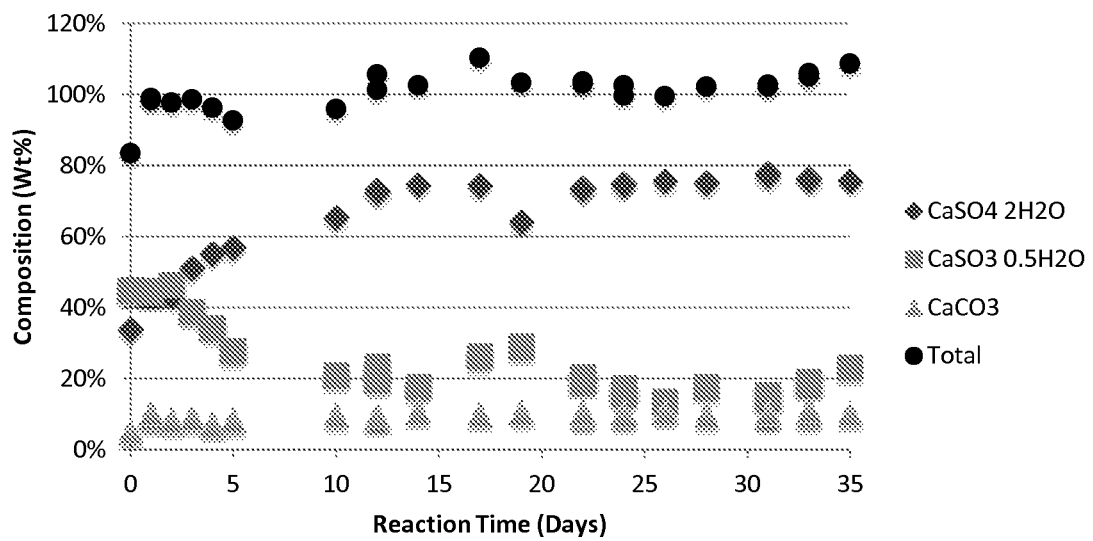
FIGS. 8A and 8B are line graphs in which are plotted sulfate ($CaSO_4 \cdot 2H_2O$; red diamonds), sulfite ($CaSO_3 \cdot \frac{1}{2}H_2O$; blue squares), and carbonate ($CaCO_3$; green triangles) composition over time as a result of bioaugmentation with added isolated SOB culture biostimulation with added SOB growth medium of FGD waste, at 32° C.
Figure 8B:
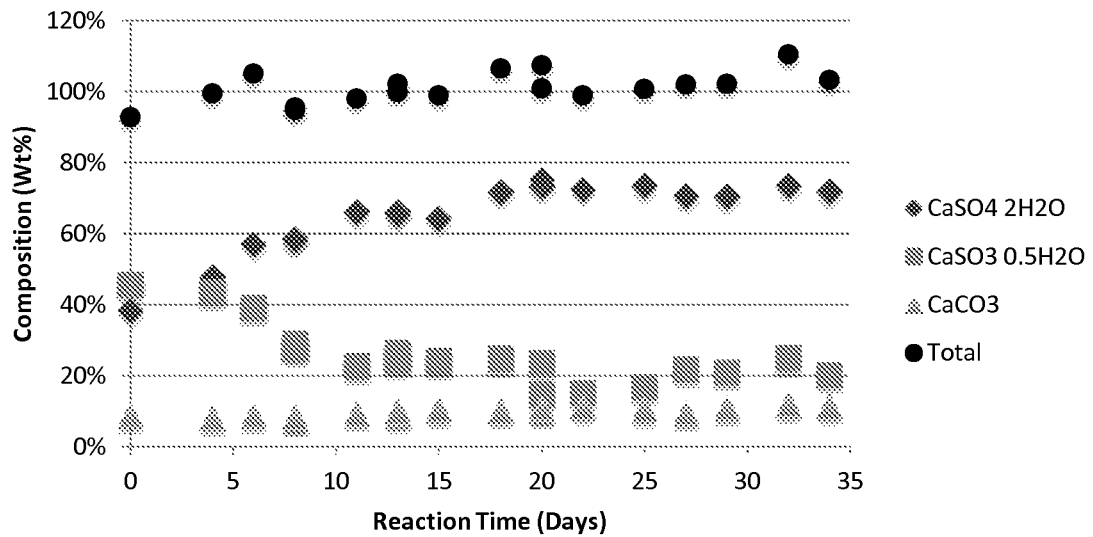

An example of the progression of treatment at two different temperatures has been plotted in FIGS. 8A and 8B. FIG. 8 is a graph in which are plotted sulfate, sulfite, and carbonate composition over time as a result of treatment of FGD waste, wherein the FGD waste was amended with an SOB growth medium to provide inorganic nutrients and the SOB bioaugmentation culture, in accordance with an embodiment of the present invention. The reaction is shown to have achieved maximum conversion sooner in the warmer treatment.

TABLE 1

Performance Summary SOB Mediated Reactions with 20% FGD Waste Slurry.

| Treatment | Initial | 24 days | Change | Initial | 24 days | Change | Initial | 24 days | Change |
|---|---|---|---|---|---|---|---|---|---|
| | $CaSO_4 \cdot 2H_2O$ (%) | | | $CaSO_3 \cdot \frac{1}{2}H_2O$ (%) | | | $CaCO_3$ (%) | | |
| Bioaugmented + Biostimulated | 38 | 74 | 36 | 46 | 17 | −26 | 9 | 11 | 2 |
| Biostimulated only | 41 | 55 | 14 | 46 | 35 | −10 | 13 | 9 | −4 |
| | Sulfate Amount (molar) | | | Sulfite Amount (molar) | | | Carbonate Amount (molar) | | |
| Bioaugmented + Biostimulated | 2.2 | 4.3 | 2.1 | 3.5 | 1.3 | −2.2 | 0.9 | 1 | 0.1 |
| Biostimulated only | 2.4 | 3.2 | 0.8 | 3.6 | 2.7 | −0.8 | 1.3 | 0.9 | −0.4 |

As Table 1 shows, merely supplementing the FGD waste slurry with SOB growth media (in the biostimulated group) results in a dramatic increase in the amount of gypsum (calcium sulfate, or $CaSO_4 \cdot 2H_2O$) that is formed over 24 days, resulting in 0.8 molar or 14% increase, and the amount of calcium sulfite ($CaSO_3 \cdot \frac{1}{2}H_2O$) was reduced by 0.8 molar (i.e., 0.8 molar decrease) (or 10%) following 24 days of supplementation of the FGD waste with SOB growth medium. However, if both SOB growth medium and isolated SOB culture are used to supplement the FGD waste, the amount of gypsum (i.e., calcium sulfate) increased by 2.1 molar (or 36%) and the amount of calcium sulfite decreased by 2.2 molar (or 26%).

Note that the results of Table 1 are more dramatic when it is understood that in FGD not supplemented with either SOB medium or isolated SOB culture, the amount of change in sulfate ($CaSO_4 \cdot 2H_2O$) and sulfite ($CaSO_3 \frac{1}{2}H_2O$) in 24 days is unchanged (i.e., 0; data not shown).

Example 2

Figures 9A, 9B:
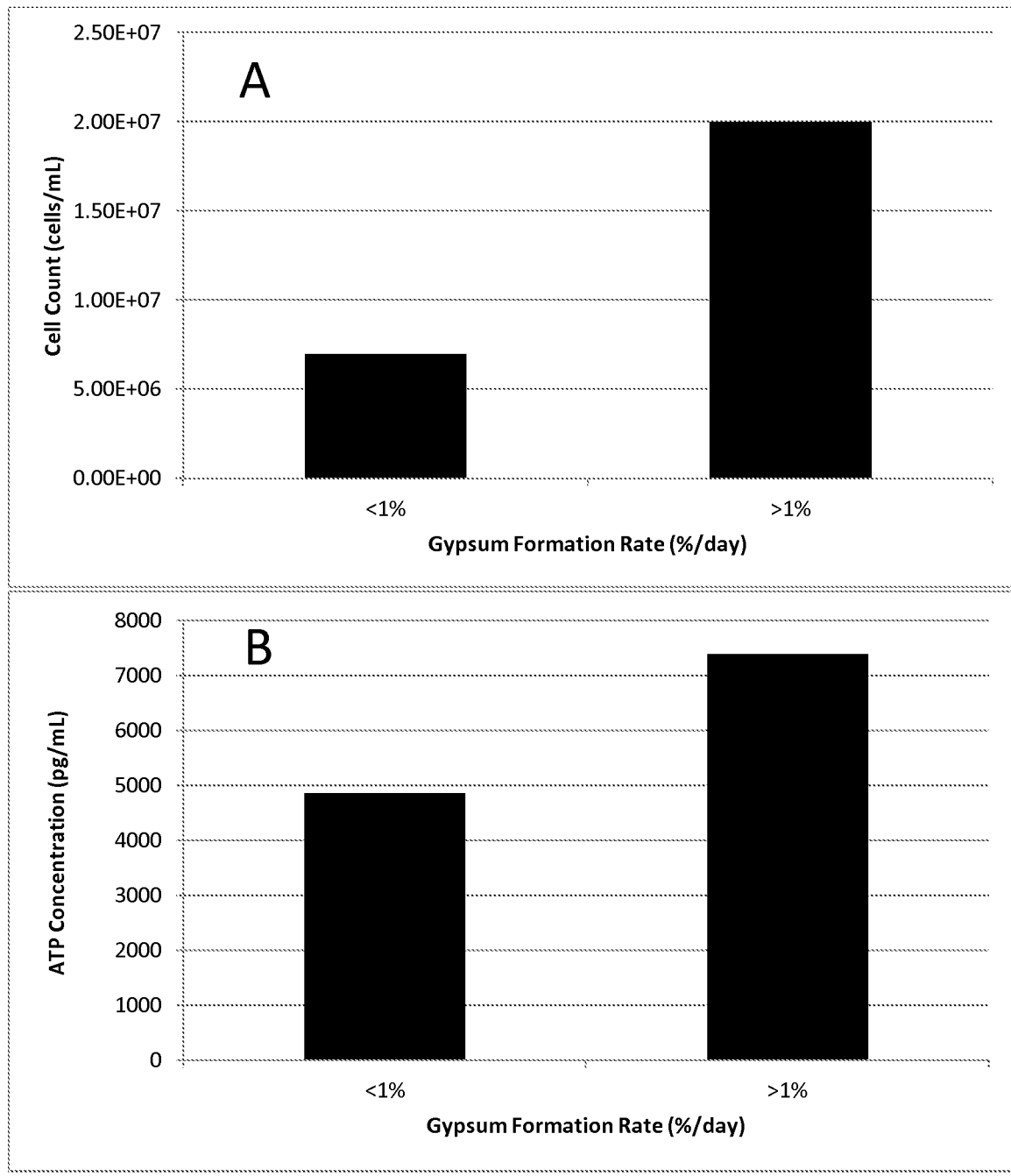
FIGS. 9A and 9B are bar graphs showing higher cell count (FIG. 9A) and ATP concentration (FIG. 9B) during gypsum enrichment in FGD waste. Thus, the amount of isolated SOB culture cells in bioaugmented, biostimulated FGD waste is directly related to the rate at which calcium sulfite hemihydrate is converted to gypsum.

This example was performed to show the superior rate of sulfite to sulfate conversion in FGD waste (to make a gypsum-enriched product) using the methods and reagents described herein. Table 2 indicates the rate of conversion that may be achieved in bioaugmented and biostimulated treatment, or treatment with biostimulation only. FIGS. 9A and 9B illustrates the benefit of SOB biomass where cell count and ATP concentration are shown to be related to the rate of gypsum formation wherein treatments forming less than 1% gypsum per day contain less biomass (lower cell counts and lower ATP; left bars of FIGS. 9A and 9B) than treatments forming more than 1% gypsum by weight per day (right bars of FIGS. 9A and 9B).

TABLE 2

Rates of SOB Mediated Reactions with FGD waste.

| | Rate of Gypsum Formation | | | Rate of Calcium Sulfite Hemihydrate Conversion | | | Rate of Calcium Carbonate Removal | | |
|---|---|---|---|---|---|---|---|---|---|
| Treatment | %/day | mg/kg · day[1] | $R^2$ | %/day | mg/kg · day[2] | $R^2$ | %/day | mg/kg · day[3] | $R^2$ |
| Bioaugmented + biostimulated | 1.61 | 16,100 | 0.91 | 1.28 | 12,800 | 0.78 | 0 | 0 | 0.73 |
| Biostimulated | 0.66 | 6600 | 0.91 | 0.50 | 5000 | 0.84 | 0.15 | 1500 | 0.99 |

[1] mg/kg · day is milligrams of gypsum formed per kilogram of FGD waste per day.
[2] mg/kg · day is milligrams of calcium sulfite hemihydrate converted to gypsum, or calcium carbonate removed per kilogram of FGD waste per day.
[3] mg/kg · day is milligrams of calcium carbonate removed per kilogram of FGD waste per day.

As in Table 1 in Example 1, Table 2 shows that merely adding SOB growth medium (not supplemented with sulfur) alone, which allows the endogenous sulfur oxidizing bacteria to increase growth, results in the increased rate of formation of sulfate, and increased rate of depletion of sulfite (i.e., by being converted into sulfate). However by adding both SOB growth medium and isolated SOB culture, a dramatic increase in the rate of formation of sulfate, and a dramatic increase in the rate of depletion of sulfite was observed. Note that the rate of carbonate removal varies according to how much carbon dioxide is available. Where carbon dioxide is available, the SOB (either the exogenously added isolated SOB culture or the endogenous SOB) will use it preferentially over carbonate. However when carbon dioxide is not available, carbonate will be used.

Thus, as Table 2 shows, when biostimulated FGD waste that has been bioaugmented with isolated SOB culture, the rate of sulfate formation goes up by almost 1% per day (i.e., 1.61% per day minus 0.66% per day equals 0.95% per day). In other words, the isolated SOB culture differs from the endogenous SOB in the FGD waste by the ability to form sulfate at a rate that is almost 250% (2.5 times) faster (i.e., 1.61 divided by 0.66 equals 2.43). Similarly, when biostimulated FGD waste that has been bioaugmented with isolated SOB culture, the rate of sulfite depletion goes up by over 0.75% per day (i.e., 1.28% per day minus 0.5% per day equals 0.78%). In other words, the isolated SOB culture differs from the endogenous SOB in the FGD waste by the ability to consume sulfite at a rate that is over 250% (2.5 times) faster (i.e., 1.28 divided by 0.5 equals 2.56). Importantly, the bioaugmentation with isolated SOB culture increases the rate of sulfate formation by the same amount as sulfite is reduced demonstrating that the source of newly formed sulfate is oxidized sulfite in the FGD waste. Thus, bioaugmentation with isolated SOB culture enhances the removal of sulfite in FGD and converts it to usable calcium sulfate (i.e., gypsum).

Example 3

This example describes the method used to derive isolated SOB culture. FGD waste product from a coal-fired generating plant is collected and made into a slurry by adding the FGD waste to sulfur-supplemented SOB growth medium. The sulfur-supplemented SOB growth medium can be prepared as follows:

10 g $Na_2S_2O_3 \cdot 5H_2O$, 3.0 g $KH_2PO_4$, 0.2 g $MgSO_4 \cdot 7H_2O$, 0.2 g $CaCl_2 \cdot 2H_2O$, 0.5 g $(NH_4)_2SO_4$, 0.02 g $MnSO_4 \cdot 2H_2O$, 0.02 g $FeSO_4$ in 1000 ml distilled water with pH 6.0.

The SOB in the FGD waste product is a consortia of bacteria containing chemolithoautotrophic sulfur oxidizing bacteria capable of oxidizing sulfite to sulfate in a mineral environment to yield an end product low in calcium sulfite. The method in this example enriches these chemolithoautotrophic sulfur oxidizing bacteria, selects the cells who have undergone random mutations to efficiently utilize the sources in the sulfur-supplemented SOB growth medium for nutrients, and selects for the appropriate bacteria cells (e.g., the chemolithoautotrophic sulfur oxidizing bacteria cells).

The waste slurry is added to a chemostat where the slurry is aerated (to provide atmospheric oxygen and carbon dioxide) in a shaker incubator at 30° C. and is repeatedly diluted over the course of several days with sulfur-supplemented SOB growth medium warmed to 30° C. until the FGD waste is essentially diluted out. The number of cells of SOB is then counted using standard methods (e.g., measuring the optical density at 595 nm wavelength, direct cell counting, or measuring ATP concentration).

The SOB are then tested to determine if they have selected and been enriched to form an isolated SOB culture. First, it is determined if the SOB culture can convert sulfite to sulfate in a sulfur-supplemented SOB growth medium at the rate of at least 0.1% (by weight) per day. Compared to endogenous SOB in the FGD slurry, the SOB is tested to see if it converts sulfite to sulfate in a biostimulated FGD slurry at least 1.5 times faster. If the SOB can convert sulfite to sulfate in a sulfur-supplemented SOB growth medium at the rate of at least 0.1% (by weight per day) and/or can convert sulfite to sulfate in a biostimulated FGD slurry at least 1.5 times faster than the endogenous SOB in a biostimulated FGD slurry, it is identified as having been selected to become an isolated SOB culture.

As the isolated SOB culture described herein have been selected to have enhanced properties to convert sulfite to sulfate, contemplated in some embodiments of the invention are kits for treating FGD waste products. Thus, in another aspect, the invention provides a kit comprising isolated SOB culture and written instruction for fostering growth of the isolated SOB culture in FGD waste product to produce a gypsum-enriched product. The written instructions can be in paper or electronic format. In some embodiments, the kit also comprises SOB growth medium. In some embodiments, the SOB growth medium is provided in desiccated form with instructions for adding water to various components of the growth medium (e.g., the ammonium source) to arrive at the SOB growth medium. The isolated SOB culture may be maintained or stored in sulfur-supplemented SOB growth medium. The kit may also comprise written instructions (e.g., in paper or electronic form) for adding the SOB growth medium (biostimulating) and adding the isolated SOB culture (bio augmenting) to the FGD waste product in accordance with the methods described herein.

In some embodiments, the kit comprises at least $1 \times 10^6$ cells of an isolated SOB culture. In some embodiments, the kit comprises at least $1 \times 10^7$ cells of an isolated SOB culture. In some embodiments, the kit comprises at least 1 liter of SOB growth medium or comprises enough components (e.g., dried $K_2HPO_4$, etc.) to make 1 liter of SOB growth medium by adding water. In some embodiments, the kit may also comprise sulfur-supplemented SOB growth medium (or dried components thereof that can be rehydrated with addition of water) for propagating the number of cells of the isolated SOB culture prior to use. Thus, the kit may also comprise written instructions (e.g., in paper or electronic form) for propagating the isolated SOB culture in the sulfur-supplemented SOB growth medium to increase the number of cells in the isolated SOB culture prior to use to treat FGD waste product.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for converting a flue gas desulfurization (FGD) waste product comprising calcium sulfite, the FGD waste product selected from the group consisting of an FGD waste-containing slurry, FGD waste in solid state, and waste-water containing FGD solids, into a gypsum-enriched product, the method comprising:
   fostering growth of sulfur oxidizing bacteria (SOB) in the FGD waste product under conditions whereby the sulfur oxidizing bacteria convert calcium sulfite in the FGD waste product to produce a gypsum-enriched product, wherein fostering growth of SOB includes supplementing the FGD waste product with chemolithoautotrophic SOB derived from FGD waste product, the FGD waste product comprising calcium sulfite and selected from the group consisting of an FGD waste-containing slurry, FGD waste in solid state, and waste-water containing FGD solids.

2. The method of claim 1, wherein fostering growth of sulfur oxidizing bacteria includes supplementing the FGD waste product with an SOB growth medium.

3. The method of claim 1, wherein the chemolithoautotrophic sulfur oxidizing bacteria derived from FGD waste product is an isolated SOB culture or a recycled sulfur oxidizing bacteria biomass from a previously treated batch of FGD waste product.

4. The method of claim 1, wherein fostering growth of sulfur oxidizing bacteria includes supplementing the FGD waste product with both an SOB growth medium and an isolated SOB culture derived from FGD waste.

5. The method of claim 4, wherein the FGD waste product is supplemented with at least $1 \times 10^7$ cells of the isolated SOB culture.

6. A method according to claim 4, wherein the isolated sulfur oxidizing bacteria culture is isolated according to a method comprising:
    obtaining a culture of chemolithoautotrophic SOB derived from FGD waste;
    propagating the culture of SOB in a sulfur-supplemented SOB growth medium for at least fifteen generations.

7. A method according to claim 6, wherein the culture is propagated in sulfur-supplemented SOB growth medium for at least twenty generations.

8. The method of claim 6, wherein the culture converts sulfite to sulfate in a sulfur-supplemented SOB growth medium at the rate of at least 0.1% per day.

9. The method of claim 6, wherein the culture converts sulfite to sulfate in a sulfur-supplemented SOB growth medium at the rate selected from the group consisting of at least 0.25% per day, at least about 0.5% per day, and at least about 0.75% per day.

10. The method of claim 6, wherein the culture converts sulfite to sulfate in a biostimulated FGD slurry at least 1.5 times faster than endogenous SOB in the FGD slurry.

11. The method of claim 6, wherein the culture converts sulfite to sulfate in a biostimulated FGD slurry at least two times faster than endogenous SOB in the FGD slurry.

12. The method of claim 1, wherein the conditions comprise fostering growth at a temperature between about 25° C. to about 35° C.

13. The method of claim 1, wherein the conditions comprise fostering growth in a presence of ammonium, phosphate, and oxygen.

14. The method of claim 1, wherein the conditions comprise a pH of between about 5 to about 8.

* * * * *